(12) United States Patent
Doubler et al.

(10) Patent No.: US 7,438,715 B2
(45) Date of Patent: Oct. 21, 2008

(54) SPINAL IMPLANT KIT

(75) Inventors: Robert L. Doubler, Ida, MI (US); John E. Hammill, Rossford, OH (US)

(73) Assignee: Spinal LLC, Toledo, OH (US)

( * ) Notice: Subject to any disclaimer, the term of this patent is extended or adjusted under 35 U.S.C. 154(b) by 346 days.

(21) Appl. No.: 11/124,455

(22) Filed: May 6, 2005

(65) Prior Publication Data

US 2006/0149255 A1     Jul. 6, 2006

Related U.S. Application Data

(63) Continuation-in-part of application No. 11/031,143, filed on Jan. 6, 2005.

(51) Int. Cl.
*A61B 17/56*     (2006.01)
*A61B 17/80*     (2006.01)

(52) U.S. Cl. .......................... 606/71; 606/280

(58) Field of Classification Search ............... 606/69–71
See application file for complete search history.

(56) References Cited

U.S. PATENT DOCUMENTS

| | | |
|---|---|---|
| 74,489 A | 2/1868 | Bidwel |
| 434,503 A | 8/1890 | Corry |
| 556,642 A | 3/1896 | Ressing |
| 824,867 A | 7/1906 | Houghton |
| 872,897 A | 12/1907 | Chapman et al. |
| 951,800 A | 3/1910 | Center |
| 1,084,680 A | 1/1914 | Wegener |
| 1,105,105 A | 7/1914 | Sherman |
| 1,907,506 A | 5/1933 | Coburn |
| 1,980,336 A | 11/1934 | Hoagland |
| 2,423,511 A | 7/1947 | Luben et al. |
| 2,757,457 A | 8/1956 | Ziegelski, Sr. |
| 3,100,516 A | 8/1963 | Nabb |
| 3,244,170 A | 4/1966 | McElvenny |
| 3,386,437 A | 6/1968 | Treace |
| 3,604,414 A | 9/1971 | Borges |
| 3,709,219 A | 1/1973 | Halloran |
| 3,741,205 A | 6/1973 | Markoff et al. |
| 3,750,652 A | 8/1973 | Sherwin |
| 3,840,014 A | 10/1974 | Ling et al. |
| RE28,841 E | 6/1976 | Allgower et al. |
| 3,960,147 A | 6/1976 | Murray |
| 4,003,376 A | 1/1977 | McKay et al. |
| 4,037,980 A | 7/1977 | Haentjens |
| 4,069,586 A | 1/1978 | Skelton |
| 4,102,339 A | 7/1978 | Weber et al. |

(Continued)

*Primary Examiner*—Cris L. Rodriguez
*Assistant Examiner*—Tara R George
(74) *Attorney, Agent, or Firm*—McHale & Slavin, P.A.

(57) ABSTRACT

A bone plate kit for stabilizing adjacent vertebrae or ends of a bone includes several bone plates of different sizes and several bone fasteners of the same or different sizes. The fasteners may have the same configuration or several different configurations. The fasteners may be coated with bone growth material. The plates have a span for extending across a discontinuity. The span has brackets for attaching to the bone. The brackets have countersunk apertures terminating through which bone screws are placed in the bone. An eccentric cam bore is located between the countersunk apertures and, upon rotation of an eccentric cam, wedge grip shoes are slid into the countersunk apertures and frictionally engage the spherical heads of the bone screws. To prevent back-out of the bone screws, the eccentric cam is locked into the wedge grip shoes.

21 Claims, 3 Drawing Sheets

U.S. PATENT DOCUMENTS

| | | |
|---|---|---|
| 4,113,227 A | 9/1978 | Cigliano |
| 4,338,926 A | 7/1982 | Kummer et al. |
| 4,388,921 A | 6/1983 | Sutter et al. |
| RE31,628 E | 7/1984 | Allgower et al. |
| 4,484,570 A | 11/1984 | Sutter et al. |
| 4,488,543 A | 12/1984 | Tornier |
| 4,493,317 A | 1/1985 | Klaue |
| 4,503,848 A | 3/1985 | Caspar et al. |
| 4,542,539 A | 9/1985 | Rowe, Jr. et al. |
| 4,651,724 A | 3/1987 | Berentey et al. |
| 4,733,657 A | 3/1988 | Kluger |
| 4,762,122 A | 8/1988 | Slocum |
| 4,794,918 A | 1/1989 | Wolter |
| 4,896,661 A | 1/1990 | Bogert et al. |
| 4,898,161 A | 2/1990 | Grundei |
| 4,943,292 A | 7/1990 | Foux |
| 4,957,495 A | 9/1990 | Kluger |
| 4,959,065 A | 9/1990 | Arnett et al. |
| 5,000,166 A | 3/1991 | Karpf |
| 5,002,544 A | 3/1991 | Klaue et al. |
| 5,019,079 A | 5/1991 | Ross |
| 5,041,113 A | 8/1991 | Biedermann et al. |
| 5,052,373 A | 10/1991 | Michelson |
| 5,053,036 A | 10/1991 | Perren et al. |
| 5,057,111 A | 10/1991 | Park |
| 5,059,194 A | 10/1991 | Michelson |
| 5,085,660 A | 2/1992 | Lin |
| 5,108,395 A | 4/1992 | Laurain |
| 5,127,912 A | 7/1992 | Ray et al. |
| 5,127,914 A | 7/1992 | Calderale et al. |
| 5,129,899 A | 7/1992 | Small et al. |
| 5,147,361 A | 9/1992 | Ojima et al. |
| 5,151,103 A | 9/1992 | Tepic et al. |
| 5,167,662 A | 12/1992 | Hayes et al. |
| 5,180,381 A | 1/1993 | Aust et al. |
| 5,190,544 A | 3/1993 | Chapman et al. |
| 5,209,751 A | 5/1993 | Farris et al. |
| 5,217,497 A | 6/1993 | Mehdian |
| 5,234,430 A | 8/1993 | Huebner |
| 5,300,073 A | 4/1994 | Ray et al. |
| 5,338,197 A | 8/1994 | Kwan |
| 5,344,457 A * | 9/1994 | Pilliar et al. ............ 606/60 |
| 5,364,399 A | 11/1994 | Lowery et al. |
| 5,380,328 A | 1/1995 | Morgan |
| 5,397,363 A | 3/1995 | Gelbard |
| 5,423,826 A | 6/1995 | Coates et al. |
| 5,456,685 A | 10/1995 | Huebner |
| 5,478,340 A | 12/1995 | Kluger |
| 5,478,348 A | 12/1995 | Bajada |
| 5,492,442 A | 2/1996 | Lasner |
| 5,520,690 A * | 5/1996 | Errico et al. ............ 606/61 |
| 5,527,314 A | 6/1996 | Brumfield et al. |
| 5,531,554 A | 7/1996 | Jeanson et al. |
| 5,531,746 A | 7/1996 | Errico et al. |
| 5,545,163 A | 8/1996 | Miller et al. |
| 5,545,165 A | 8/1996 | Biedermann et al. |
| 5,549,612 A | 8/1996 | Yapp et al. |
| 5,558,674 A | 9/1996 | Heggeness et al. |
| 5,562,663 A | 10/1996 | Wisnewski et al. |
| 5,562,672 A | 10/1996 | Huebner et al. |
| 5,578,034 A | 11/1996 | Estes |
| 5,601,553 A | 2/1997 | Trebing et al. |
| 5,603,713 A | 2/1997 | Aust et al. |
| 5,607,426 A | 3/1997 | Ralph et al. |
| 5,616,142 A | 4/1997 | Yuan et al. |
| 5,616,144 A | 4/1997 | Yapp et al. |
| 5,643,265 A | 7/1997 | Errico et al. |
| 5,662,652 A | 9/1997 | Schafer et al. |
| 5,672,175 A | 9/1997 | Martin |
| 5,676,666 A | 10/1997 | Oxland et al. |
| 5,676,703 A | 10/1997 | Gelbard |
| 5,735,853 A | 4/1998 | Olerud |
| 5,735,899 A | 4/1998 | Schwartz et al. |
| 5,755,796 A | 5/1998 | Ibo et al. |
| 5,766,254 A | 6/1998 | Gelbard |
| D402,032 S | 12/1998 | Stone |
| 5,849,012 A | 12/1998 | Abboudi |
| D406,646 S | 3/1999 | Stone |
| 5,876,402 A | 3/1999 | Errico et al. |
| 5,876,446 A | 3/1999 | Agrawal et al. |
| 5,954,722 A | 9/1999 | Bono |
| 6,022,350 A | 2/2000 | Ganem |
| 6,030,389 A | 2/2000 | Wagner et al. |
| 6,152,927 A | 11/2000 | Farris et al. |
| 6,224,602 B1 | 5/2001 | Hayes |
| 6,231,610 B1 | 5/2001 | Geisler |
| 6,342,055 B1 | 1/2002 | Eisermann et al. |
| 6,398,783 B1 | 6/2002 | Michelson |
| 6,436,142 B1 | 8/2002 | Paes et al. |
| 6,454,771 B1 | 9/2002 | Michelson |
| 6,669,700 B1 | 12/2003 | Farris et al. |
| 6,730,127 B2 | 5/2004 | Michelson |
| 6,740,088 B1 | 5/2004 | Kozak et al. |
| 6,893,444 B2 | 5/2005 | Orbay |
| 6,936,051 B2 | 8/2005 | Michelson |
| 2004/0102773 A1 | 5/2004 | Morrison et al. |
| 2005/0187551 A1 | 8/2005 | Orbay et al. |
| 2005/0283152 A1* | 12/2005 | Lindemann et al. ........ 606/61 |
| 2006/0106387 A1* | 5/2006 | Fanger et al. ............ 606/69 |

* cited by examiner

SPINAL IMPLANT KIT

RELATED APPLICATIONS

This application is a continuation in part of U.S. patent application, Ser. No. 11/031,143 filed Jan. 6, 2005, which is incorporated herein by reference.

FIELD OF THE INVENTION

This invention relates to the field of orthopedic surgery and to kits, eg., surgical trays, including bone plates and screws or other fastening devices by which the plates are secured to the bone.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma.

The interface between the bone screws and the bone presents problems of stability and long term usage that have been addressed in different ways. One of the major problems is usually termed as back-out. This defines the condition in which the fastening devices attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contributes greatly to the problem.

Spinal bone plates are usually attached to adjacent vertebrae to reduce pain due to injury or deterioration of the intermediate disk. The plate spans the intervertebral space to stabilize the vertebrae. Pedicle screws or bone screws are inserted through apertures in the opposite ends of the plate into the respective vertebrae or on opposite sides of a break. Due to anatomical forces on the skeleton, the screws sometimes back out of the bones and plates.

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface. Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

Published application, US 2004/0102773 A1, to Morrison et al, uses the ends of the bone plate to cover the heads of the bone screws.

U.S. Pat. No. 6,740,088 B1, to Kozak et al uses extra set screws to interfere with the heads of the bone screws.

U.S. Pat. No. 6,730,127 B2 to Michelson attaches an overlay to the plate to partially cover the heads of the screws.

What is needed in the art is a bone plate kit with several different types of bone fasteners to provide a choice in securement with each of the fasteners adapted to cooperate with an internal sliding screw lock that rotates to wedge the bone fasteners to the plate.

SUMMARY OF THE PRESENT INVENTION

The surgical kit is composed of one or more bone plate(s) for stabilizing adjacent vertebrae and several different fasteners for penetrating and securing the plate(s) to bone assembled together in a package. The apertures through the plate(s) and the heads of the fasteners are of commensurate size to allow for flexibility in choice of fasteners.

The plate is formed from a span of rigid material for bridging intervertebral space, the span having a bone engaging surface and a distal surface. A first bracket is located at one end of the span and a second bracket is located on the other end of the span. The first bracket includes a first bone fastener aperture and a second bone fastener aperture therethrough with a cam bore between the first bone fastener aperture and the second fastener aperture. A slot in the first bracket extends from the first bone fastener aperture to the second bone fastener aperture with an eccentric cam rotatably mounted in the cam bore, the cam includes a cam surfaces. A first wedge shoe is slidably disposed in the slot between the cam and the first bone fastener aperture for contacting the cam surface. A second wedge shoe is slidably disposed in the slot between the cam and the second bone fastener aperture for contacting the cam surfaces. A cam cover plate can be used to close the slot whereby rotating the cam slides te first and second wedge shoe partially into the first and second bone fastener aperture.

Therefore, it is an objective of this invention to provide a bone plate kit containing several bone plates of different sizes and a series of bone fasteners of different configurations with the bone plates and the fasteners of a size and shape to cooperate in securing a plate to a patient.

It is another objective of this invention to provide a bone plate with an integral internal screw lock.

It is still another objective of this invention to provide a spinal plate with sliding wedge shoes.

It is yet another objective of this invention to provide a low profile bone plate with countersunk bone fastener apertures therethrough having wedge shoe openings.

It is a further objective of this invention to provide a coating for the fasteners that promotes incorporation of the fastener in the bone.

Other objectives and advantages of this invention will become apparent from the following description taken in conjunction with the accompanying drawings wherein are set forth, by way of illustration and example, certain embodi-

DETAILED DESCRIPTION OF THE INVENTION

Figure 1:
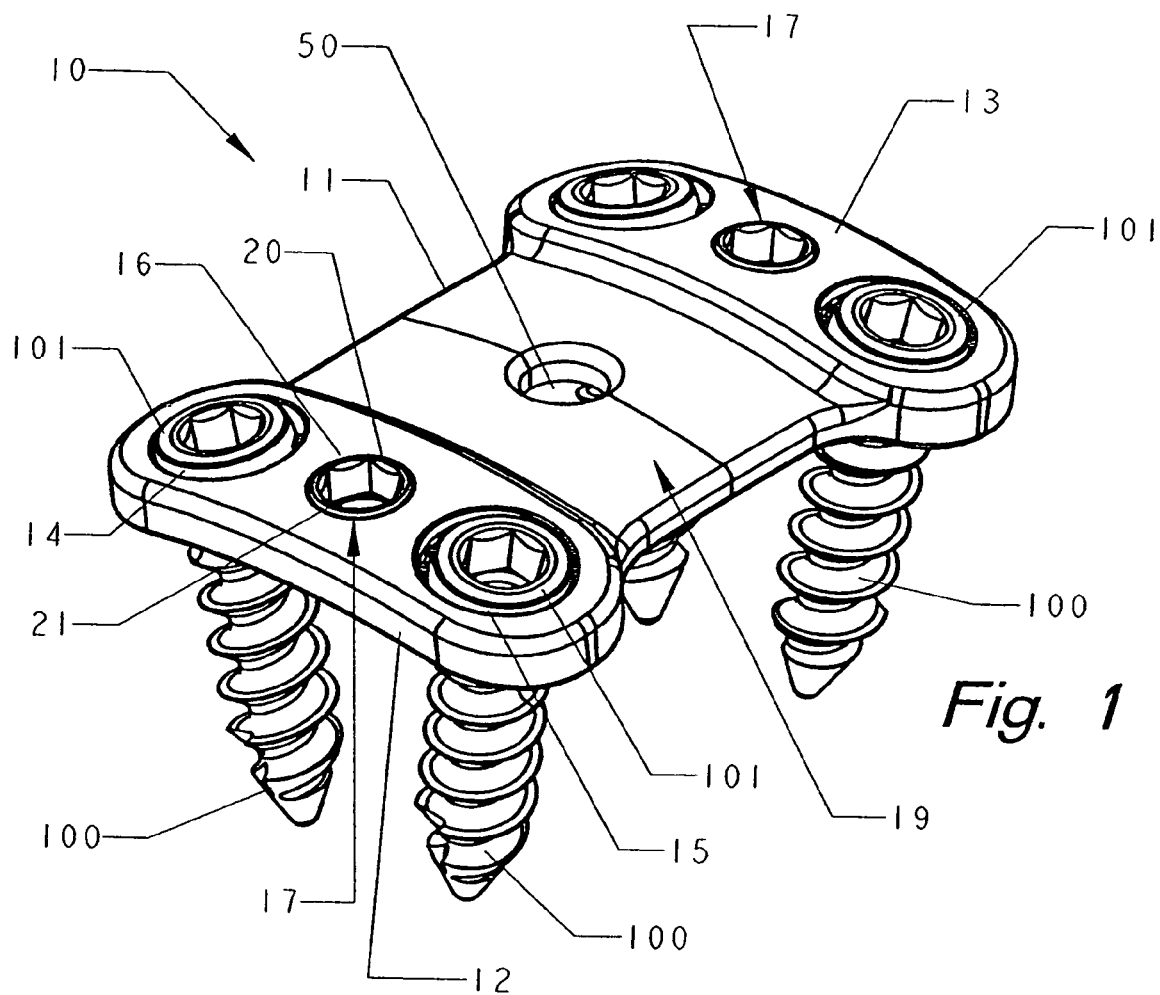
FIG. 1 is a perspective distal side of an assembled bone plate and screw threaded fasteners of this invention.
Figure 2:
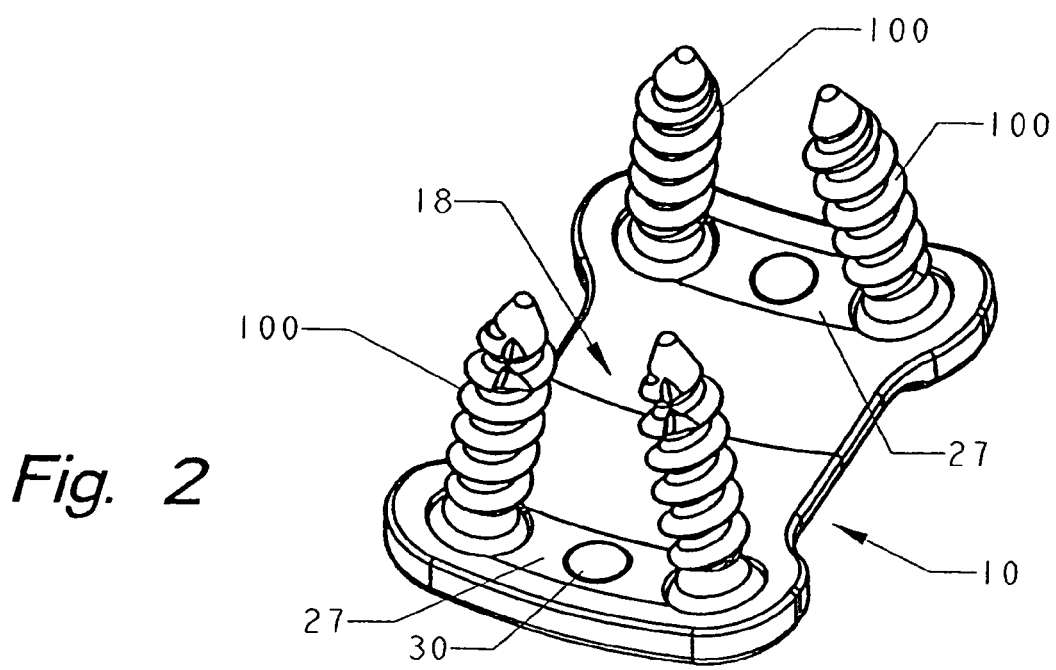
FIG. 2 is a perspective of bone engaging side of the bone plate and screw threaded fasteners of this invention.
Figure 4:
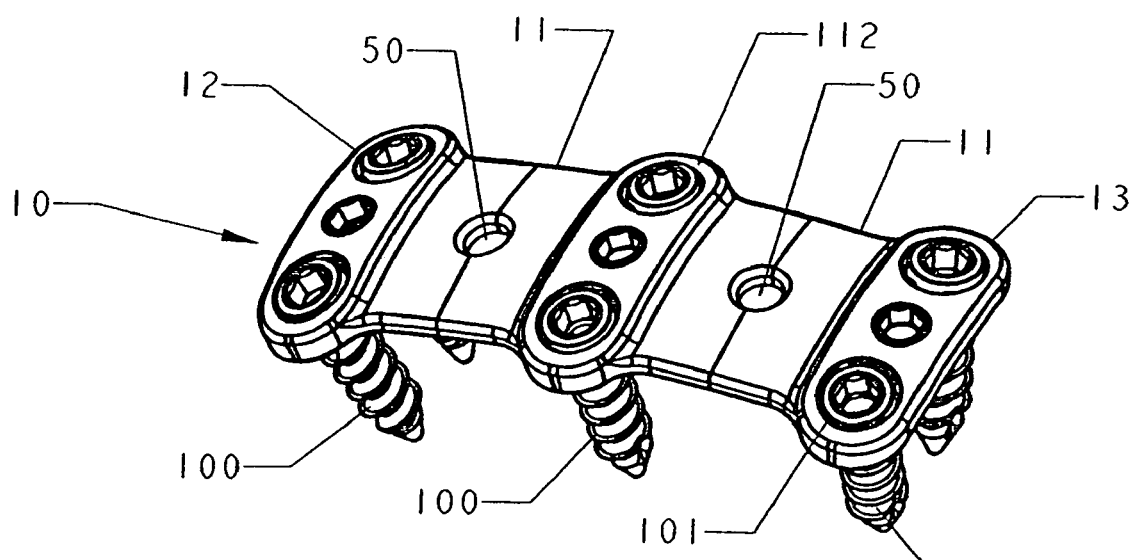
FIG. 4 is a perspective of another embodiment of the bone plate of this invention.
Figure 8:
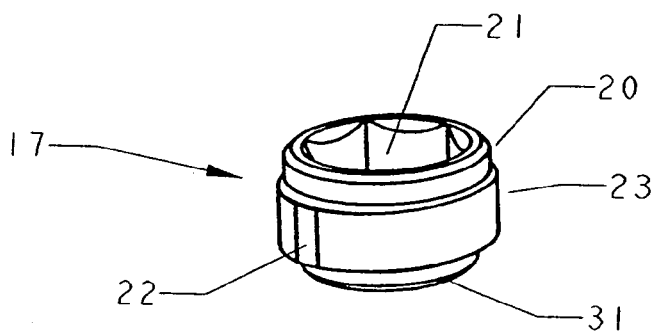
FIG. 8 is a perspective of the eccentric cam.

The bone plate 10, shown in FIGS. 1, 2, and 4, is based on an elongated span 11 having a first end and a second end with a first bracket 12 on the first end adapted to engage a first vertebrae and a second bracket 13 on the second end adapted to engage a second vertebrae. The first bracket includes a first bone fastener aperture 14 and a second bone fastener aperture 15 with a cam bore 16 located therebetween, each bone fastener aperture being countersunk. Screw threaded fasteners 100 are shown in place with the screw heads 101 resting in the countersunk apertures. This contributes to the low profile of the implant preventing undue trauma to the tissue on the anterior aspect of the cervical spine. A rotating eccentric cam 17, shown in FIG. 8, is mounted in the cam bore.

The second bracket 13 has the same components as the first bracket 12. An aperture 50 is located in the span 11 to facilitate boney ingrowth to increase stability. In FIG. 4, a bone plate 10 is shown with an intermediate bracket 112 which also includes all the elements of the bracket 12. Of course, the bone plate may have a series of brackets spaced apart by multiple spans for use when several vertebrae or bone fragments are to be stabilized.

The bone plate has two major surfaces, a bone engaging surface 18 and a distal surface 19. The bone fastener apertures and the cam bores extend through the bone plate from the bone engaging surface to the distal surface. The cam bore 16, in the distal surface 19, is circular and serves as a guide and bearing surface for the distal end of the actuator 20 of the eccentric cam 17. The actuator has a receptacle 21 for a tool (not shown) used to rotate the cam. The actuator 20 terminates on the distal surface to preserve the smooth surface.

Eccentric cam surfaces 22 and 23 are formed 180° apart on the shaft of the cam 17. In the unlocked position, the cam surfaces are aligned with the longitudinal axis of the span 11. By turning the actuator 90°, the cam surfaces 22 and 23 are aligned transverse to the axis of the span.

Figure 3:
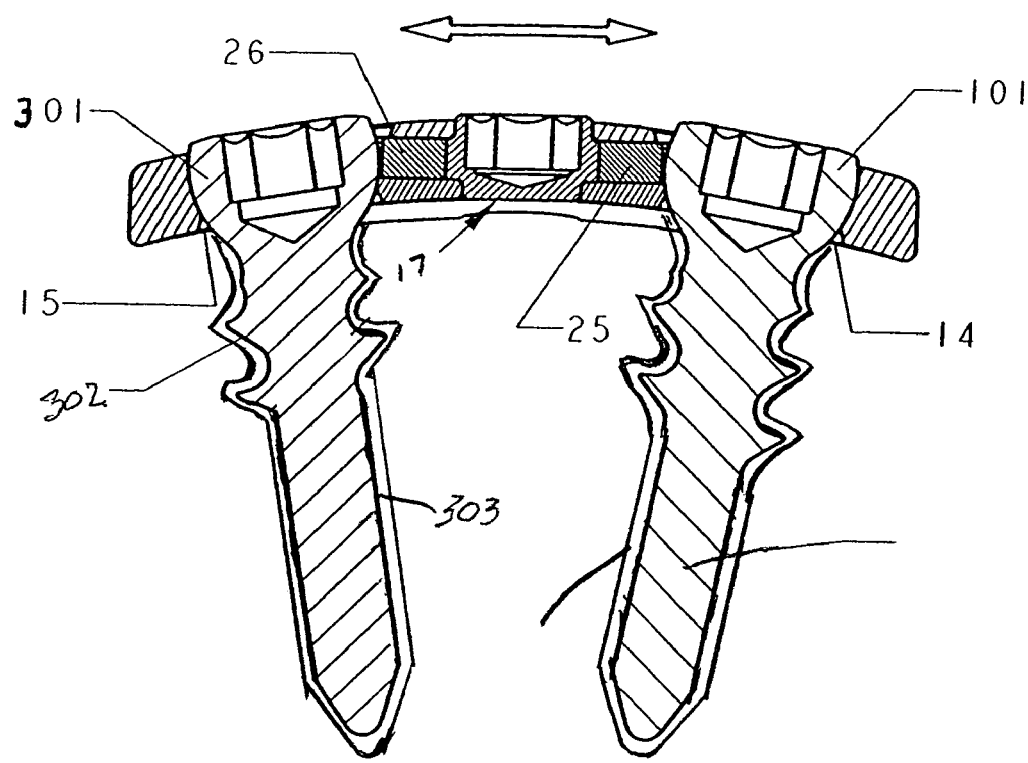
FIG. 3 is a transverse cross section of a bone plate of this invention with coated cortical thread fasteners.
Figure 7:
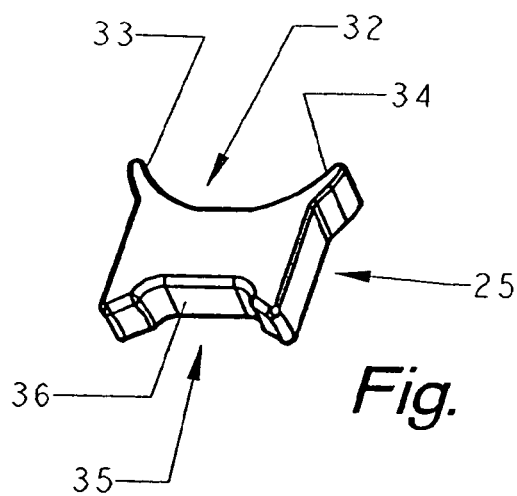
FIG. 7 is a perspective of a wedge show.
Figure 6:
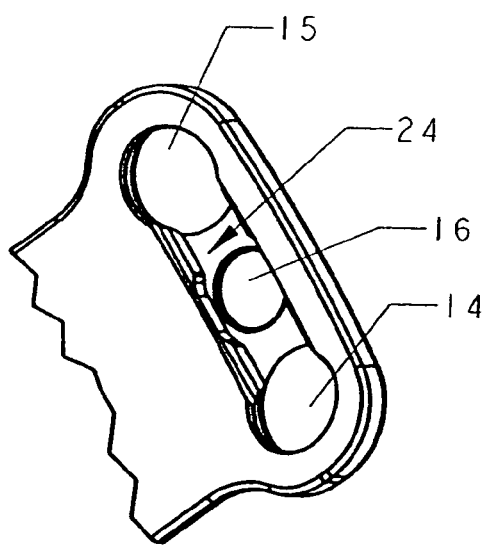
FIG. 6 is a partial perspective of the wedge show recess.

As shown in FIGS. 2, 3, and 6, each of the brackets have an internal slot 24 extending transversely between the countersunk apertures 14 and 15. The cam shaft penetrates the center of the slot. A wedge grip shoe 25, as shown in FIG. 7, is slidably disposed in the slot between the cam shaft and the aperture 14. Another wedge grip shoe 26 is slidably disposed in the slot between the cam shaft and aperture 15.

Figure 9:
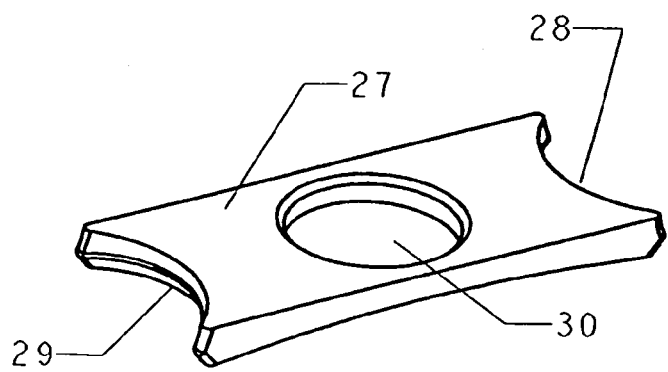
FIG. 9 is a perspective of the cam cover plate.

A cam cover plate 27, as shown in FIG. 9, closes each slot and forms the bone engaging surfaces of the brackets of the bone plate. The cam cover plate extends transversely along the brackets between the screw apertures. Each end 28 and 29 of the covers has an arcuate shape conforming to the shape of the countersunk aperture. A cam bore 30 passes through the plate and serves as a guide and bearing surface for the other end 31 of the eccentric cam 17. The cam cover plates are permanently attached to the brackets, as by laser welding or other fastening method.

One end 32 of the wedge grip shoes 25 is shaped to conform generally with the head of the fastener, as shown in FIG. 3, but including contact points 33 and 34 near the sides of the shoes to insure more than one positive pressure point about the circumference of the head. The other end 35 of the shoes is shaped with an indentation 36 to act as a lock to prevent the eccentric cam from reversing rotation. More specifically, the cam surfaces 22 and 23 of the rotating cam 17 cooperate with the indentation 36 on the shoes to act as a lock to prevent rotation of the cam with respect to the wedge shoe.

Figure 5:
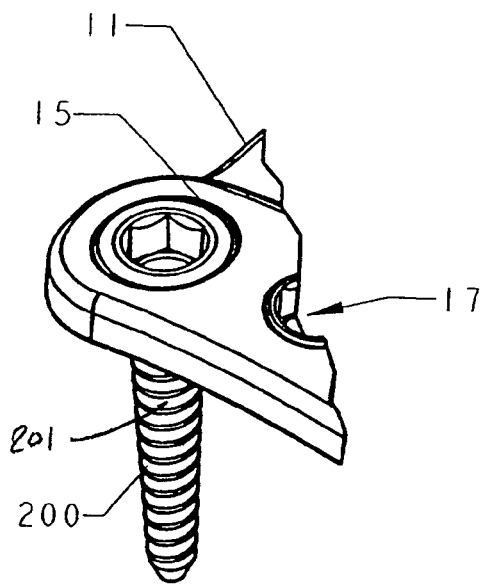
FIG. 5 is a partial perspective of the bone plate of this invention with a pin.

Pins 200, shown in FIG. 5, may be used instead of or in place of the screw threads or other bone fasteners. The pins 200 have several spaced apart raised circular rings 202 rather than the helical threads of a screw. The rings 202 provide more purchase with the bone than a smooth pin and allow bone growth to fill the space between the rings. The pin head 201 is commensurate in size with the countersunk fastener apertures 14, 15 in the bracket 12. All of the heads of the fasteners 100, 200 and 300 in the kit are of a size and shape to cooperate with the fastener apertures of the plate(s) so that when seated in the countersunk apertures there is a smooth low profile exterior surface. However, the kit may contain fasteners of different lengths and diameters with the same size head. Also, all or some or none of the fasteners may be coated with a material 303 to promote bone growth, eg., BMP, bone morphogenic proteins, DBM, demineralized bone matrix, any bone marrow aspirate, platelet rich plasma, compositie ceramic hydroxyapatite, tricalcium phosphate, glass resin mixtures, resorbable highly purified polylactides/polylactides-co-glycolides and others. The kit allows the surgeon to choose the best fastener for the surgical situation.

The bone fastener 300 has a cortical thread 302 which may approximate, in length, the depth of the hard exterior of a bone. The remainder of the shank may be smooth. This configuration provides maximum purchase in the bone with minimum disruption of the bone marrow.

The heads of the bone fasteners have a spherical shape as do the countersunk portions of the brackets, as shown in FIG. 3. This allows for some flexibility in placement of the plate and fasteners to compensate for anatomical considerations or to gain better purchase in the bone. When the bone screws or pins have been fully tightened, the eccentric cam is rotated by the actuator. The cam surfaces engage the wedge grip shoes and slide each toward the countersunk apertures. At 90° the cam surfaces are disposed in the indentations of the shoes and cannot freely return to the original position. The other ends of the shoes have moved into the countersunk portion of the apertures and engage the circumference of the spherical heads at least at two points. The surface of the countersunk bores opposite the wedge shoes serves as a reaction surface to secure the fasteners from backing out of the bone.

The bone plate and fasteners may be fabricated from surgical steel, titanium, other suitable alloys, ceramics alone or as coatings, and polymers or combinations thereof with the requisite strength and nontoxicity in the body.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A bone plate kit for implanting a bone plate across discontinuities in skeletal bone, said kit comprising a bone plate and a plurality of bone fasteners, said bone plate including an elongated span having a first end and a second end, said first end defining a first bracket and said second end defining a second bracket, said first and said second bracket each having at least two apertures adapted to receive said bone fasteners, said first bracket and said bracket each having an internal slot therein extending between said at least two apertures, at least two wedge shoes slidably disposed in each said internal slot, each said wedge shoe adjacent one of said apertures, a rotatable cam disposed within said internal slot and positioned between said two wedge shoes, said rotatable cam having a cam surface constructed and arranged to contact a first end of each said wedge shoe, said first end of each said wedge shoe is shaped to cooperate with a surface of said cam to lock said cam in a position whereby rotation of said cam with respect to said wedge shoe is substantially prevented, rotation of said cam causes substantially linear traversal of each said wedge shoe along said internal slot to frictionally engage a side surface of said bone fasteners received in said at least two adjacent apertures in an amount effective to prevent substantial hone fastener rotation.

2. A bone plate kit of claim 1 comprising an intermediate bracket on said elongated span between said first end and said second end, said intermediate bracket having at least one bone fastener aperture, said bone fasteners each having a head of a size and shape approximating said at least one aperture, an eccentric cam adjacent said aperture, an internal slot in said intermediate bracket extending from said eccentric cam to said aperture, a wedge shoe slidably disposed in said internal slot, said internal slot formed from a cam cover plate securing said cam and said wedge shoes within said internal slot, one end of said wedge shoe contacting said eccentric cam whereby rotation of said eccentric cam extends said wedge shoe into said aperture.

3. A bone plate kit of claim 2 comprising a second aperture in said intermediate bracket, said eccentric cam located between said one and said second apertures, said bone fasteners each having a head of a size and shape approximating said second aperture, said internal slot extending between said one and said second apertures, a second wedge shoe in said internal slot between said eccentric cam and said second aperture whereby rotation of said eccentric cam slides said wedge shoe and said second wedge shoe partially into said one and said second apertures, respectively.

4. A bone plate kit of claim 3 comprising a spherical head on said each of said plurality of fasteners, said counter sunk bore having a spherical shape, respectively, said first and said second wedge shoe including one end adapted to engage said bone fastener, respectively, said one end shaped to substantially conform with said bone fastener.

5. A bone plate kit of claim 2 comprising a countersunk bore surrounding said aperture in said intermediate bracket, said bore having a sidewall, said wedge shoe extending through said countersunk bore.

6. A bone kit of claim 1 comprising a countersunk surrounding each said aperture, said bore having a sidewall, said wedge shoe extending through said countersunk bore.

7. A bone plate kit of claim 1 comprising a bone growth promoting material coated on at least one of said fasteners.

8. A bone plate kit for stabilizing adjacent vertebrae comprising a span for bridging an intervertebral space, said span having a bone engaging surface, a distal surface, a first end and a second end, a first bracket on said first end of said span and a second bracket on said second end of said span, said first bracket having a first bone fastener aperture for receipt of a first bone fastener and a second bone fastener aperture for receipt of a second bone fastener therethrough, a cam bore between said first bone fastener aperture and said second bone fastener aperture, a substantially linear slot in said first bracket extending from said first bone fastener aperture to said second bone fastener aperture, an eccentric cam rotatably mounted in said cam bore and having cam surfaces, a first wedge shoe slidably disposed in said slot between said cam and said first bone fastener aperture and contacting said cam surfaces, a second wedge shoe slidably disposed in said slot between said cam and said second bone fastener aperture and contacting said cam surfaces, each said first and said second wedge shoe having a first end and a second end, a cam cover plate closing said slot forming an internal slot, said first end of each said wedge shoes is shaped to cooperate with one of said cam surfaces to lock said cam in a position whereby rotation of said cam with respect to said wedge shoe is substantially prevented, rotating said cam slides said first and said second wedge shoe along said substantially linear slot to frictionally engage a said surface of said bone fasteners in an amount effective to prevent substantial bone fastener rotation.

9. A bone plate kit of claim 8 comprising a countersunk bore surrounding said bone-fastener aperture, said bore having a sidewall, said wedge shoe extending through said countersunk bore.

10. A bone plate kit of claim 9 comprising a spherical head on said each of said plurality of fasteners, said counter sunk bore having a spherical shape, respectively.

11. A bone plate kit of claim 8 comprising a cortical screw thread on a portion of a shank of at least one of said bone fasteners.

12. A bone plate kit of claim 11 comprising a series of circular rings on a shank of at least one of said fasteners.

13. A bone kit of claim 11 comprising a helical screw thread on a shank of at least one of said fasteners.

14. A bone kit of claim 13 comprising a series of circular rings on a shank of at least one of said fasteners.

15. A bone plate kit of claim 8 comprising a helical screw thread on a shank of at least one of said bone fasteners.

16. A bone plate kit of claim 8 comprising a series of circular rings on a shank of at least one of said fasteners.

17. A bone plate kit of claim 8 comprising a bone growth promoting material coated on at least one of said fasteners.

18. A bone plate kit of claim 8 comprising several bone plates, said bone plates of different sizes, said several bone plates each having fastener apertures of the same size.

19. A bone plate kit of claim 8 further including said second bracket having a first bone fastener aperture and a second bone fastener therethrough, a cam bore between said first bone fastener aperture and said second bone fastener aperture, a substantially linear slot in said second bracket extending from said first bone fastener to said second bone fastener aperture, an eccentric cam rotatably mounted in said cam bore having cam surfaces, a first wedge shoe slidably disposed in said slot between said cam and said first bone fastener aperture and contacting said cam surfaces, a second wedge shoe slidably disposed in said slot between said cam and said second bone fastener aperture and contacting said cam surfaces, a cam cover plate closing said slot forming an internal slot whereby rotating said cam slides said first and said second wedge shoes along said substantially linear internal slot to frictionally engage a side surface of said bone fasteners in an amount effective to prevent substantial bone fastener rotation.

20. A bone plate kit for stabilizing adjacent vertebrae comprising a first bracket defining a first end of a bone plate, said bone plate including at least one bone fastener aperture therethrough for accepting a bone fastener, a first cam aperture spaced from and substantially parallel to said at least one bone fastener aperture, a first cam rotatably secured within said first cam aperture, a substantially linear internal slot extending between said first cam aperture and said at least one bone fastener aperture, said internal slot constructed and arranged to guide a first wedge shoe, said first wedge shoe having a first wend and a second end, said first end adapted to engage a bone fastener located in said at least one bone fastener aperture, said second end adapted to engage an eccentric surface of said first cam, whereby rotation of said cam causes substantially linear traversal of said first wedge shoe along said internal slot to prevent substantial rotation of said bone fastener, a second bracket defining a second end of said bone plate, said second bracket including at least one bone fastener aperture therethrough for accepting a second bone fastener, a second cam aperture spaced from and substantially parallel to said at least one bone fastener aperture, a second cam rotatably secured within said second cam aperture, a substantially linear internal slot extending between said second cam aperture and said at least one bone fastener aperture, said internal slot constructed and arranged to guide a second wedge shoe, said second wedge shoe having a first end and a second end, said second end adapted to engage said second bone fastener located in said at least one bone fastener aperture, said first end adapted to engage an eccentric surface of said second cam, whereby rotation of said second cam causes substantially linear traversal of said second wedge shoe along said internal slot to prevent substantial rotation of said second bone fastener.

21. The bone plate kit of claim 20 including a third bracket defining a middle portion of said bone plate, said third bone plate including at least one bone fastener aperture therethrough for accepting a third bone fastener, a third cam aperture spaced from and substantially parallel to said at least one bone fastener aperture, a third cam rotatably secured within said third cam aperture, a substantially linear internal slot extending between said third cam aperture and said at least one bone fastener aperture, said internal slot constructed and arranged to guide a third wedge shoe, said third wedge shoe having a first end and a second end, said second end adapted to engage said third bone fastener located in said at least one bone fastener aperture, said second end adapted to engage an eccentric surface of said third cam, whereby rotation of said third cam causes substantially linear traversal of said third wedge shoe along said internal slot to prevent substantial rotation of said third bone fastener.

* * * * *